(12) United States Patent
Li et al.

(10) Patent No.: US 8,765,031 B2
(45) Date of Patent: Jul. 1, 2014

(54) METHOD OF FORMING A DENTAL APPLIANCE

(75) Inventors: Chunhua Li, Cupertino, CA (US); Yan Chen, Cupertino, CA (US)

(73) Assignee: Align Technology, Inc., San Jose, CA (US)

( * ) Notice: Subject to any disclaimer, the term of this patent is extended or adjusted under 35 U.S.C. 154(b) by 590 days.

(21) Appl. No.: 12/583,062

(22) Filed: Aug. 13, 2009

(65) Prior Publication Data

US 2011/0039223 A1     Feb. 17, 2011

(51) Int. Cl.
  *B29C 51/02* (2006.01)
  *A61C 7/08* (2006.01)

(52) U.S. Cl.
  USPC .................................. 264/16; 264/294; 433/6

(58) Field of Classification Search
  None
  See application file for complete search history.

(56) References Cited

U.S. PATENT DOCUMENTS

| | | | | |
|---|---|---|---|---|
| 5,324,186 | A * | 6/1994 | Bakanowski | 425/116 |
| 5,449,703 | A * | 9/1995 | Mitra et al. | 522/57 |
| 6,390,812 | B1 * | 5/2002 | Chishti et al. | 433/6 |
| 6,441,354 | B1 * | 8/2002 | Seghatol et al. | 219/679 |
| 6,705,861 | B2 | 3/2004 | Chishti et al. | |
| 7,354,270 | B2 | 4/2008 | Abolfathi et al. | |
| 7,985,414 | B2 * | 7/2011 | Knaack et al. | 424/422 |
| 2006/0292520 | A1 | 12/2006 | Dillon et al. | |
| 2007/0122592 | A1 * | 5/2007 | Anderson et al. | 428/156 |

OTHER PUBLICATIONS

Prime, R. Bruce. "An Introduction to Thermosets". http://www.primethermosets.com, Accessed Aug. 13, 2009 (8 pgs,).

* cited by examiner

*Primary Examiner* — Benjamin Schiffman
(74) *Attorney, Agent, or Firm* — Brooks, Cameron & Huebsch, PLLC

(57) ABSTRACT

The present disclosure includes dental appliances and methods of making and using such appliances. One method for forming a dental appliance includes forming a liquid thermoset polymer material into a semi-solid first shape, thermoforming the semi-solid first shape of thermoset polymer material onto a dentition mold, and curing the thermoset polymer on the dentition mold with a curative trigger to complete a molecular cross-linking reaction.

24 Claims, 10 Drawing Sheets

METHOD OF FORMING A DENTAL APPLIANCE

BACKGROUND

The present disclosure is related generally to the field of dental treatment. More particularly, the present disclosure is related to the fabrication of polymeric dental appliances for orthodontic dental treatment.

Many dental treatments involve repositioning misaligned teeth and changing bite configurations for improved cosmetic appearance and dental function. Repositioning can be accomplished, for example, by applying controlled forces to one or more teeth over a period of time. Repositioning teeth for aesthetic or other reasons has been accomplished by wearing what are commonly referred to as "braces." Braces typically encompass a variety of hardware such as brackets, archwires, ligatures, and O-rings.

Some dental processes use polymeric dental positioning appliances, rather than braces, for realigning teeth. Such appliances may, for example, utilize a thin shell of material having resilient properties, referred to as an "aligner" that generally conforms to a patient's teeth but is slightly out of alignment with the present (e.g., initial) tooth configuration. Placement of such an appliance over the teeth provides controlled forces in specific locations to gradually move the teeth into a new configuration. Repetition of this process with successive appliances that provide progressive configurations eventually move the teeth through a series of intermediate arrangements to a final desired arrangement.

Many processes for forming such dental appliances utilize thermoplastic material. These materials have a long period in which the forming of the dental appliance can take place, and therefore are desirable materials.

DETAILED DESCRIPTION

Figures 1A, 1B, 1C:
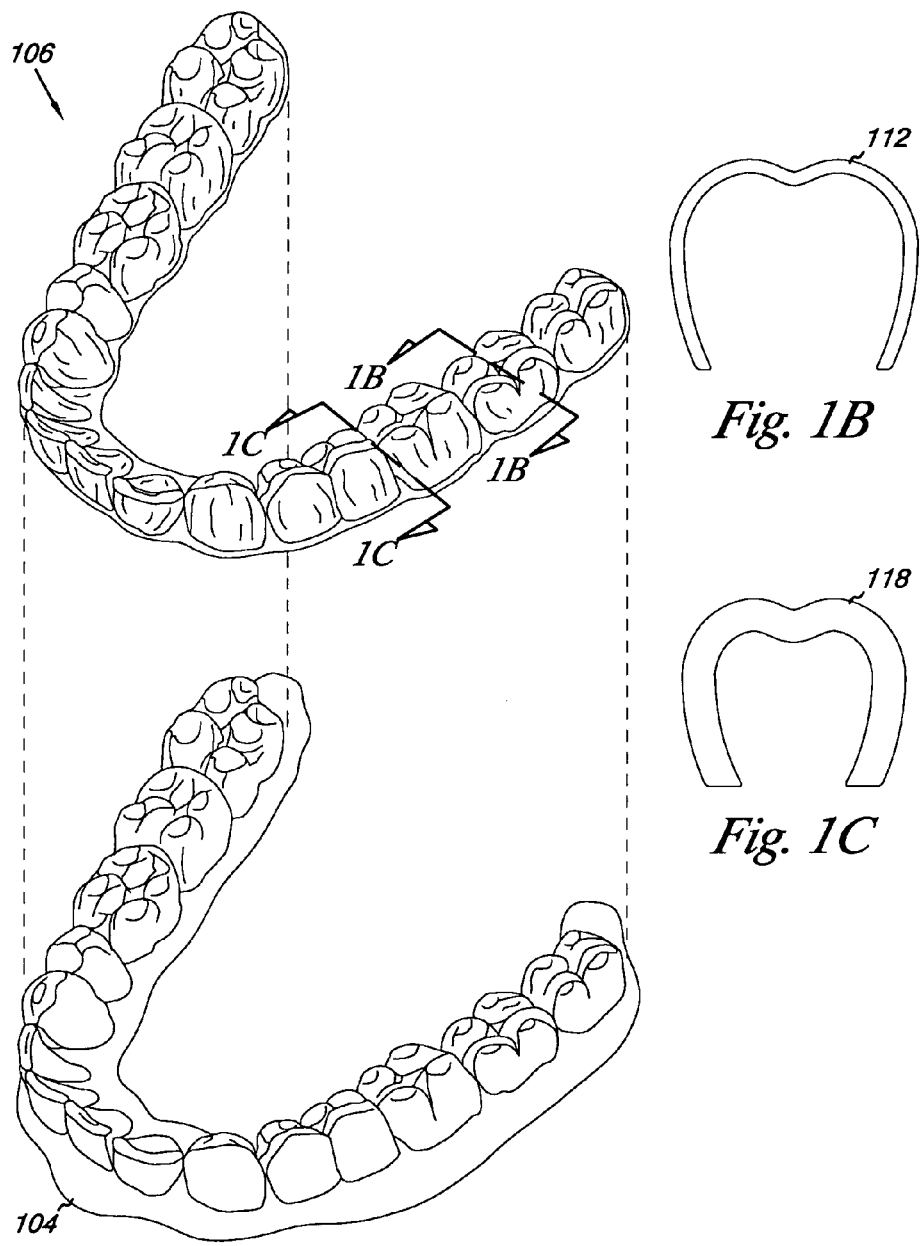
FIG. 1A illustrates a jaw including patient's teeth and an embodiment of a dental appliance to treat a dental condition of the patient according to the present disclosure.
FIG. 1B illustrates a dental appliance cross section as taken along line 1B-1B of FIG. 1A.
FIG. 1C illustrates a dental appliance cross section as taken along line 1C-1C of FIG. 1A.

Embodiments of the present disclosure provide dental appliances and methods of making and using such appliances. In various embodiments, for example, a method embodiment for forming a dental appliance is described that includes partially curing a thermoset polymer material into a formable first shape. This method embodiment further includes thermoforming the first shape of thermoset polymer material onto a dentition mold, and fully curing the thermoset polymer on the dentition mold to complete a molecular cross-linking reaction.

In various embodiments, a dentition of the patient's teeth can be formed in a number of ways. For example, an impression of the patient's teeth can be taken to form the dentition.

In some instances, one or more digital models can be created and used to form the dentition. For example, the patient's teeth or the dentition created from the patient's teeth can be digitally scanned and the data manipulated to form dentitions used for repositioning teeth or for application of materials (e.g., chemical treatments) to the patient's teeth.

For instance, a digital model can be used to fabricate a dental appliance corresponding to a present, anticipated, and/or desired configuration of the patient's dentition through analysis and/or manipulation of the data set forming the digital model. Additional detail on the use of digital modeling can be found in commonly assigned U.S. patent application Ser. No. 12/283,770, filed on Sep. 16, 2008, entitled "Dental Condition Evaluation and Treatment".

A series of dental appliances, e.g., "aligners," generally rely on designing and fabricating some, most, or all of the appliances, to be worn by the patient over time, at the outset of treatment, or while treatment is occurring. In some processes, the design of the appliances uses computer modeling of a series of successive tooth arrangements and the individual appliances are designed to be worn over the teeth and to reposition the teeth by using the appliances in a serial order, progressing from a first appliance, through each of the intermediate appliances, to the last appliance. An example of a dental treatment system, including a series of dental appliances, e.g., "aligners," is described in commonly-assigned U.S. Pat. No. 5,975,893, which is incorporated herein in its entirety.

Dental aligners have been made of thermoplastic polymers, since this category of polymer can be easily thermoformed into a desired aligner configuration. For example, a sheet of thermoplastic polymer material can be heated over a mold in order to conform the thermoplastic polymer material to the shape of the mold. The mold may be of an existing configuration of a patient's teeth, or of an intended future configuration.

However, in some implementations, thermoplastic polymer materials tend to fatigue over time, particularly under constant loading, such as in orthodontic treatment applications. Thermoplastic polymer materials may also tend to deform over time due to stress relaxation of material, and/or material fatigue in some instances.

In some applications, aligner deformation can reduce force delivered to the teeth for some orthodontic movements, and thus, can provide inconsistent application of force throughout a particular course of treatment with a given aligner. In such applications, the fatigue and/or deformation limitations associated with thermoplastic polymer materials may limit the magnitude of movement that can be obtained from a particular aligner, or the time over which a particular aligner may be utilized.

In the embodiments described in the present disclosure, aligners can be molded using a thermoset polymer material. As used herein, a thermoset polymer material includes those polymeric materials that once shaped by applied energy (e.g., heat, pressure, radiation), or chemical reaction, so as to form a cross-linked polymeric matrix, are incapable of being reprocessed into a different form by further application of the particular energy.

That is, aligners can be molded using a category of polymers that are irreversibly cured in the desired aligner configuration. Examples of thermoset polymer materials include castable/casting polyurethane, acrylate curable polymers, silicone thermoset polymers and elastomers, and epoxy polymers, among others.

An aligner is formed to a patient's teeth, or to programmed dentitions (e.g., intermediate teeth configurations of a proposed orthodontic treatment plan). An aligner formed using thermoset polymer materials is capable of capturing the details of a particular dentition, either by intermediate thermoforming over the dentition, or by another suitable process. Several examples of methods for forming a dental appliance (e.g., an aligner) using thermoset polymer materials are provided below.

FIG. 1A illustrates a jaw including patient's teeth and an embodiment of a dental appliance to treat a dental condition of the patient according to the present disclosure. The devices, methods, or systems of the present disclosure can be, or employ, any manner of positioners, trays, retainers, and/or other removable dental appliances. The systems for use in various embodiments of the present disclosure can utilize a single appliance, or a plurality of such appliances that can, for example, be worn by a patient successively in order to achieve the gradual tooth repositioning, as described herein.

Accordingly, embodiments of the present disclosure are not limited to an "aligner" that is intentionally fabricated slightly out of alignment with the present tooth configuration so as to provide force to one or more teeth. As will be appreciated, a dental appliance according to embodiments of the present disclosure may conform to a patient's tooth configuration. Thus, according to at least one embodiment of the present disclosure, treatment targeted at a particular tooth, several teeth, and/or the gingiva can be accomplished concurrent with alignment treatment (e.g., tooth position adjustment), or separate and distinct from the alignment treatment.

The present disclosure also includes one or more method embodiments for forming (e.g., casting) a dental appliance. For example, one such method embodiment includes delivering a fluid (e.g., liquid, viscous mass) thermoset polymer precursor to a first mold having an internal cavity.

The internal cavity has a surface corresponding to an external surface of the dental appliance. The method further includes placing a second mold in proximity to the first mold such that a volume for the thermoset polymer precursor remains therebetween, the second mold being a positive dentition mold having an external surface corresponding to an internal surface of the dental appliance, and curing the thermoset polymer precursor with energy to complete a molecular cross-linking reaction, e.g., cause molecules of the thermoset polymer precursor to irreversibly link into a rigid three dimensional structure.

In various apparatus embodiments, a tooth position adjustment dental appliance is produced according to a method set forth above, the dental appliance having cavities shaped to receive and resiliently reposition teeth from a first arrangement to a second arrangement. For example, a dental appliance can include a shell having a number of cavities to receive one or more teeth formed of cross-linked polymer materials. In some embodiments, the shell is formed of thermoset polymer materials.

In one or more apparatus embodiments, the dental appliance is an aligner (e.g., shell) having a number of cavities to receive one or more teeth. The aligner is one of a series of aligners corresponding to intermediate steps of an orthodontic treatment where the number of cavities are arranged to reposition the one or more teeth from a first configuration to a successive configuration, and the aligner is fabricated from material that is irreversibly cured to irreversibly link molecules into a rigid three dimensional structure.

A dental appliance 106 (e.g., a dental positioning appliance such as an aligner, a tray for delivery of chemicals in proximity to the teeth or gums, etc.) can include a number of cavities for receiving one or more corresponding teeth. In various embodiments, the cavities can correspond to one, or multiple, teeth, implants, and/or other features of a patient's jaw.

Embodiments of the present disclosure include dental appliances, such as aligners for orthodontic positioning of one or more teeth, formed from thermoset polymer materials. In contrast to thermoplastics, thermoset polymer materials tend to fatigue less over time when placed under constant loading, such as in orthodontic treatment applications. Thermoset polymer materials deform less over time due to stress relaxation of material, and material fatigue, thereby maintaining the force delivered to the teeth for orthodontic movements for a longer period, and providing more consistent application of force throughout a particular course of treatment.

Embodiments of the present disclosure are described in relation to the accompanying drawings, which will at least assist in illustrating the various features of the various embodiments. In the Figures, the first digit of a reference number refers to the Figure in which it is used, while the remaining two digits of the reference number refer to the same or equivalent parts of embodiment(s) of the present disclosure used throughout the several figures of the drawing. The scaling of the figures does not represent precise dimensions and/or dimensional ratios of the various elements illustrated herein.

The dental appliance 106 may be designed to fit over a number of, in many instances all teeth, present in an upper or lower jaw. Dental appliances can be configured to apply force to reposition one or more teeth from a first configuration of the teeth to a successive configuration of the teeth, used in application of medication or other beneficial materials in proximity to one or more teeth and/or the gums, or used to hold teeth in place, among other such uses.

In some embodiments, certain individual teeth, or small sets of the teeth, can be repositioned while one or more other the teeth provide a base or anchor region for holding the repositioning appliance in place as it applies a resilient repositioning force against the tooth or teeth to be repositioned. Some embodiments can have repositioning portions, anchor portions, and/or portions that cover a portion of a tooth or teeth but do not provide any force to the covered tooth or teeth.

In various embodiments, one or more cavities of the dental appliance are formed in an oversized manner with respect to the teeth over which it is to be applied (e.g., by scaling-up) for chemically treating one or more certain teeth. For example, one or more chemicals (e.g., medications) or other materials may be applied to the interior surface of the appliance due to the scaled up nature of this appliance's fabrication.

FIG. 1B illustrates a dental appliance cross section 112, as taken along line 1B-1B of FIG. 1A. FIG. 1C illustrates a dental appliance cross section 118, as taken along line 1C-1C of FIG. 1A. As illustrated, the dental appliance can have a U-shaped cross-section to form one or more cavities for placement of a patient's teeth therein. Such a shape can be formed, for example, by placement of a partially cured thermoset polymer material over a dentition mold (e.g., forming the inner surface).

Thermoset polymer material can be classified as uncured, partially cured, or cured (i.e., fully cured). Uncured thermoset polymer material describes unreacted resin (e.g., A-stage of cure). Fully cured thermoset polymer material describes thermoset polymer material having complete molecular cross-linking reaction, so as to irreversibly cross-link molecules into a rigid three dimensional structure (e.g., C-stage of cure). Partially cured thermoset polymer material describes thermoset polymer material between uncured and fully cured stages of cure (e.g., sometimes called the green phase or B-stage of cure).

Figure 2A:
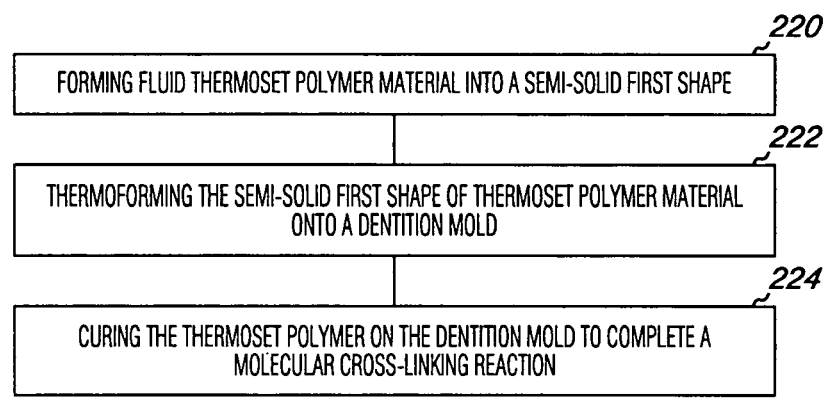
FIG. 2A is a block diagram illustrating a method for fabricating a dental appliance according to an embodiment of the present disclosure.

FIG. 2A is a block diagram illustrating a method for fabricating a dental appliance according to an embodiment of the present disclosure. According to one or more embodiments, a method for forming a dental appliance includes forming and partially curing a liquid thermoset polymer material into a semi-solid first shape at 220. The method further includes thermoforming the semi-solid first shape of thermoset polymer material onto a dentition mold at 222, and curing the thermoset polymer on the dentition mold with energy, or chemical reaction, to complete a molecular cross-linking reaction at 224.

A wide range of processing techniques may be used for forming, or partially curing, the liquid thermoset polymer material into a semi-solid first shape, including molding, extrusion, rolling, etc. Some suitable processing techniques for producing the first shape include compression molding, such as is used to make precision parts; liquid injection molding, for example using low pressure in conjunction with a bottom fill mold; and reaction injection molding with high pressure impingement mixing. Other suitable processing techniques may also be used, including, but not limited to: open casting; centrifugal molding, including pipelining, making of sheet goods and use of multi-cavity molds; ribbon flow moldless casting where the first shape is formed using rollers rather than a mold; transfer molding, such as is used to make multiple precision parts; rotational molding, often used to make hollow items; vacuum casting, as may be used to make wire or fiber inserts; pressure casting utilizing a pressure chamber; B-staging used when the shape of particular molds create difficulty in holding liquids; spray; solvent casting involving low pressure for fabric penetration; and dipping for materials having a sufficiently long working life which may be heat activated; among others.

Figure 2B:
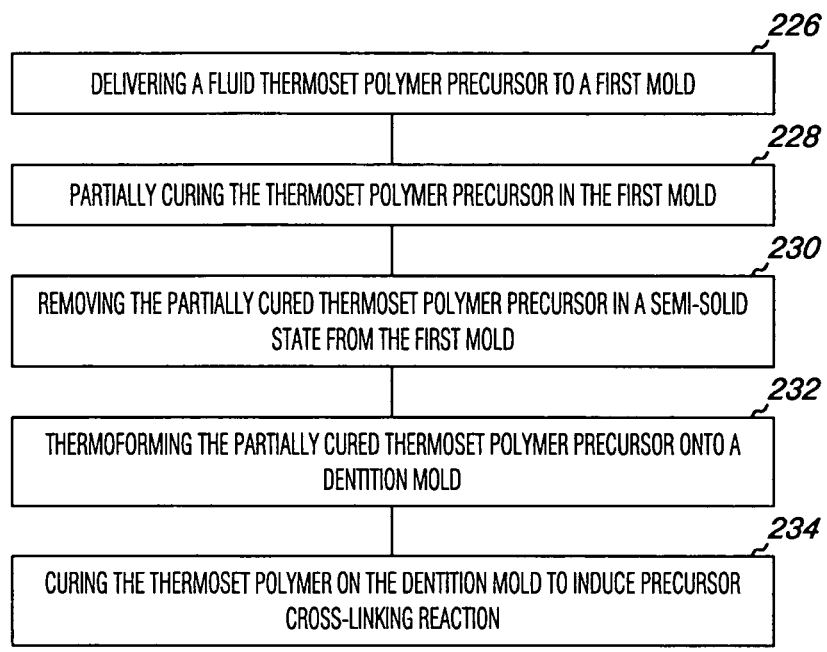
FIG. 2B is a block diagram illustrating another method embodiment for fabricating a dental appliance according to the present disclosure.

FIG. 2B is a block diagram illustrating another method embodiment for fabricating a dental appliance according to the present disclosure. According to one or more embodiments, a method for forming a dental appliance includes delivering a fluid thermoset polymer precursor to a first mold (e.g., to form a sheet or shell, for example) at 226, partially curing the thermoset polymer precursor in the first mold at 228, removing the partially cured thermoset polymer precursor in a semi-solid state from the first mold at 230, thermoforming the partially cured thermoset polymer precursor onto a dentition mold at 232, and curing the thermoset polymer precursor on the dentition mold with energy to induce a cross-linking reaction at 234.

One example of a method embodiment such as that described in FIG. 2B includes two or more urethane prepolymer components being prepared and mixed with one or more curatives to initiate a chemical reaction of the urethane prepolymer components. The thermoset polymer precursor is cast, or molded, into a preliminary configuration (e.g., sheet, shell), and partially cured.

As the thermoset polymer precursor begins to solidify into thermoset polymer material, but while the sheet is still not fully cured (e.g., a semi-solid state), it is often referred to as being in a "green" phase. The green phase sheets may be removed from the cast, or mold, and used to fabricate a dental appliance (e.g., an aligner) such as by thermoforming the green phase sheet onto a negative dentition mold of the intended configuration (e.g., 104 in FIG. 1A). Thereafter (e.g., after forming into an aligner configuration), the dental appliance can be further (e.g., fully) cured.

In some embodiments, the dental appliance is formed using green phase material that is further cured by exposure to a curative trigger. The curative trigger can be one or more of energy (e.g., light, heat, radiation), force (e.g., pressure), or chemical reaction. After forming (e.g., applied to a mold), the green phase material can be exposed to the curative trigger for some period of time to allow the formed dental appliance to substantially cure as a thermoset polymer material. However, embodiments of the present disclosure are not limited to exposing the green phase material to a curative trigger after forming in order to obtain substantial curing.

In some embodiments, a dental appliance may be formed after exposure of the green phase material to a curative trigger (e.g., at an appropriate time during curing as the thermoset polymer precursor transitions to being substantially cured as a thermoset polymer material). That is, curing may be initiated as a result of a chemical reaction, and at some window of time during the curing process, the partially cured materials are removed from a preliminary configuration mold, thermoformed onto a dentition, and allowed to continue curing thereon, without further exposure to a curative trigger (e.g., energy, force, chemical, or other trigger).

According to one or more embodiments, a method for forming a dental appliance does not include forming green phase stock used for further forming into a dental appliance. Rather, a dental appliance is fabricated directly from the thermoset polymer precursor materials.

For example, curable polymers can be mixed with the desired components and initiators. This thermoset polymer precursor can then be directly injected into a positive dentition mold, and allowed to partially cure in the mold.

In this manner, a partially cured dental appliance can be formed directly. This partially cured dental appliance aligner can be further cured (e.g., fully), in the mold or after removal from the mold, by application of energy such as radiation, light, heat, pressure, or some combination thereof, to complete the cross-linking reaction. Again, further curing is not limited by input of additional energy, and can also occur without additional application of additional energy or other curative trigger (e.g., force).

In some embodiments, the dental appliance can be molded of a thermoset polymer material, as discussed herein. As will be appreciated, the dental appliance can be placed within a molding tool and the thermoset polymer precursor can be supplied to the molding tool to form the dental appliance. Supplying the thermoset polymer precursor can, for example, include injecting a fluid thermoset polymer precursor, and an optional catalyst, into the mold under low pressure to fill the mold cavity volume.

Since the thermoset polymer precursor can have a low viscosity, the thermoset polymer precursor can substantially fill spaces defined by various surfaces of the dental appliance. A curative trigger (e.g., pressure, one or more chemicals, light and/or heat that causes the thermoset polymer to finally cure) can then be applied to cure the thermoset polymer precursor to form the dental appliance.

In some embodiments, a method for molding a dental appliance includes placing a mold having an internal cavity, where the internal cavity includes a first portion and a second portion, at a first position so that the second portion is in a higher relative position than the first portion. Also, a thermoset polymer precursor can be injected through the mold into the first portion of the internal cavity to partially fill the internal cavity.

Once the thermoset polymer precursor has been injected, the mold can be moved from a first position to a second position to reorient the first portion and the second portion so the first portion is in a higher relative position than the second portion. The thermoset polymer precursor can then be injected through the mold into the second portion of the internal cavity to at least partially fill the internal cavity.

After partial or substantially complete curing, the dental appliance can be removed from the mold. A post cure process can also be used.

As will be appreciated, a variety of molding processes exist that can be used to form the dental appliances. Examples of such molding processes can include thermoset polymer precursor transfer molding, compression molding, and injection molding, among others.

In various embodiments, the dental appliance could be formed in a casting process or stamping process. In one or more embodiments, portions (e.g., layers, sections) of a dental appliance can be individually formed (e.g., cast, molded) and subsequently coupled together to form the dental appliance. Examples of suitable techniques for coupling the individual portions include use of natural or synthetic adhesives and/or thermal energy to join the individual portions together.

As provided herein, thermoset polymer materials can be formed from the cross-linking (e.g., polymerization) of one or more thermoset polymer precursor(s). In the embodiments described herein, the thermoset polymer precursor can be selected from an unsaturated polyester, a polyurethane, an epoxy, an epoxy vinyl ester, a phenolic, a silicone, an alkyd, an allylic, a vinyl ester, a furan, a polyimide, a cyanate ester, a bismaleimide, a polybutadiene, and a polyetheramide, among other suitable thermoset polymer materials. In one embodiment, the thermoset polymer precursor includes resin in an A-stage of cure (i.e., unreacted resin).

As will be appreciated, the thermoset polymer material used in the embodiments of the present disclosure can also include reinforcement materials and/or additives such as one or more fillers, wires, fibers, curing agents, inhibitors, catalysts, and toughening agents (e.g., elastomers), among others, to achieve a desirable combination of physical, mechanical, chemical, and/or thermal properties. Reinforcement materials can include woven and/or nonwoven fibrous materials, particulate materials, and/or other high strength materials.

Examples of reinforcement materials can include, but are not limited to, synthetic fibers, natural fibers, and ceramic fibers. Fillers include materials added to the matrix of the thermoset polymer material to alter its physical, mechanical, thermal, or chemical properties. Such fillers can include, but are not limited to, organic and inorganic materials, clays, silicates, mica, talcs, rubbers, fines, and paper, among others.

In one or more embodiments, the classes of thermoset polymer materials are biocompatible (e.g., thermoset polyurethanes, silicone rubbers, and acrylics such as methyl methacrylate (MMA) and polyethene glycol dimethacrylate (PEGDMA) copolymer). Embodiments can use a material that is mechanically and/or chemically stable in a saliva environment. In some embodiments, it is beneficial for the thermoset polymer material to be chemically resistant to teeth cleaning materials.

As will be appreciated, the thermoset polymer precursor can be formed into the thermoset polymer material by a polymerization reaction initiated and cured through heat, pressure, chemical reaction with catalysts, ultraviolet light, irradiation (e.g., electron beam processing), and/or other types of energy. The curing process transforms the thermoset polymer precursor into the thermoset polymer by a cross-linking process.

Energy or catalysts may be added that cause the molecules to react at chemically active sites, linking the molecules into a rigid three-dimensional structure. The cross-linking process forms a molecule with a relatively larger molecular weight, resulting in a material having a higher melting point. The polymerization reaction increases the molecular weight such that the material solidifies, and will burn rather than melt at elevated temperatures.

In one or more embodiments, the thermoset polymer material of the present disclosure can have at least one percent (1%) cross-linking network structure. This improves the structural characteristics of the material for a dental appliance application in some instances, as discussed further below.

The thermoset polymer material can have clarity characteristics ranging from opaque to clear (e.g., transparent). The thermoset polymer material can be non-colored or colored (e.g., include colored agents), which thereby may provide shading ranging from a colored opaque to a tinted transparent, or further to a clear transparent.

As previously discussed, polymeric dental positioning appliances can be used for aligning teeth. Such appliances may, for example, utilize a thin shell of material having resilient properties that generally conforms to a patient's teeth but is slightly out of alignment with the patient's teeth. Placement of such an appliance over the teeth provides controlled forces in specific locations to gradually move the teeth into a new configuration.

Therefore, the material used to fabricate the polymeric dental positioning appliances (e.g., an aligner) needs to have a tensile strength such that when the material is deformed over an initial tooth configuration, sufficient force may be transferred to the tooth, or teeth, causing the deformation. Since deformation of the polymeric dental positioning appliance is used to create the forces applied to a tooth, or teeth, the material should be capable of elongation without breakage, have sufficiently large tensile and flexural moduli, and/or have stress relaxation characteristics that allow for the generation of force by resilient opposition to deformation.

In one or more embodiments, the thermoset polymer material can have one or more of the following characteristics: a tensile strength at yield of greater than 6,000 pounds per square inch (psi), an elongation at yield of greater than ten percent (10%), an elongation at break of greater than eighty percent (80%), a tensile modulus at secant one percent (1%) greater than 100,000 psi, a flexural modulus greater than 100,000 psi, and stress relaxation in 37° C. and one hundred percent (100%) relative humidity over 24 hours of more than twenty percent (20%).

Dental appliances fabricated using thermoset polymer material, such as those having one or more of the above-mentioned characteristics, can be more resilient than that of thermoplastic polymers. Due to the cross-linked structure, thermoset polymer materials can retain their original shape better and/or longer than thermoplastic polymers, and thereby maintain application of a relatively more consistent force when used to achieve orthodontic tooth movement. As will be appreciated, fabricating dental appliances using thermoset polymer materials that retain their original shape better and/or longer can improve dental appliance performance, such as over a given treatment time of a particular dental appliance (e.g., 2-3 weeks for some aligner embodiments), since material fatigue is reduced.

Less material fatigue results, for example, in a more constant force being delivered by a dental appliance formed with a thermoset polymer material. Using a dental appliance fabricated of thermoset polymer material for orthodontic treatment can also result in more predictable outcomes (e.g., teeth movement) with respect to original programmed movements in some instances. Increasing predictability through better controlled force application can reduce treating professional intervention to correct a teeth configuration that does not match expected results.

Improved performance can also support longer treatment periods and/or greater tooth movement distance, and thus, fewer intermediate aligners between an initial and final teeth position, may be utilized in some instances. In turn, fabrication costs may be reduced for some treatment plans, since fewer dental appliances may be needed.

Figure 3:
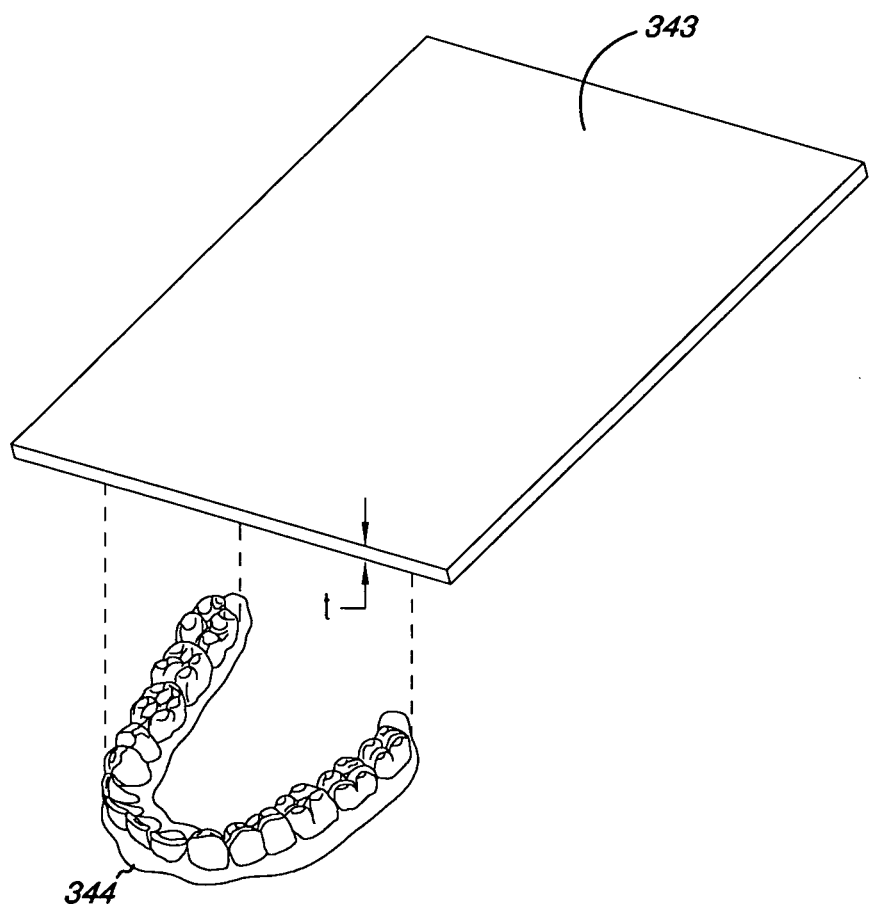
FIG. 3 illustrates an embodiment of a first shape with respect to a dentition according to the present disclosure.

FIG. 3 illustrates an embodiment of a first shape 343 with respect to a dentition 344 according to the present disclosure. According to one or more embodiments, the first shape 343 can be formed to be substantially flat, such as into a semi-solid sheet of partially cured thermoset polymer material, for example.

The first shape 343 can be formed to have a substantially constant thickness, or non-uniform thickness, (e.g., t as shown in FIG. 3). The thickness of the first shape may, for example, be based on jaw size or crown height, crown height being the dimension of a tooth measured from the junction between the enamel of the crown and the dentine of the roots, to the occlusal surface, as will be understood by one having ordinary skill in the art. For instance, a thicker first shape may provide more material, e.g., greater volume, to thermoform over a larger jaw size, e.g., larger dentition molds. For example, relatively larger dental appliances can also be provided with a thicker first shape 343, since the first shape 343 may be stretched more in forming a larger sized dental appliance relative to a smaller size dental appliance.

Non-uniform thickness can, for example, be utilized to provide a more uniform final thickness to a dental appliance, as in some instances, the thickness of the material may change as the appliance is formed. Accordingly, sections that typically get thinner during formation of the dental appliance, can be provided with an extra thickness during formation of the first shape 343. In some embodiments, extra thickness can be used to reinforce some areas of the appliance. For example, in some areas, the extra thickness can be used to provide extra force and/or rigidity to a particular area of the appliance.

Non-uniform thickness can, for example, vary in the range of 10-30 mil.; however, embodiments of the present disclosure are not limited to this range, and thickness may vary more, or less, than the above-mentioned range. According to one or more embodiments, a green phase first sheet is fabricated to include a non-uniform thickness across the first sheet in the range of 20-30 mil., the thickness at any particular point on the first sheet such that after forming the dental appliance has a uniform thickness of 20 mil.

To achieve uniform thickness after forming and curing, areas of the first sheet that will be subject to stretching and/or thinning by bending during forming of the dental appliance over a mold may be fabricated to have a greater thickness than areas of the first sheet that will not be subject to such localized forming forces. The reader will appreciate, that areas of the first sheet corresponding to transitions during forming into a final dental appliance, can be formed to have a greater thickness in the first sheet to accommodate the change in thickness during the forming transition.

The first sheet can be fabricated to have non-uniform thickness, such that a dental appliance formed from the first sheet having the non-uniform thickness, will also have non-uniform thickness. For example, it may be desired to have an occlusal area of a dental appliance (after forming) to have a different thickness than a gingival area of the dental appliance. It may also be desired, depending on the forces needed to move particular teeth, to have one area of the dental appliance have a different thickness than another area of the dental appliance. These areas of different thickness in the final dental appliance may be achieved, at least in part, by forming the dental appliance using a green phase first sheet fabricated to have a non-uniform thickness across the first sheet (e.g., the first sheet being thicker in areas corresponding to areas of the dental appliance desired to have greater thickness).

Figure 9:
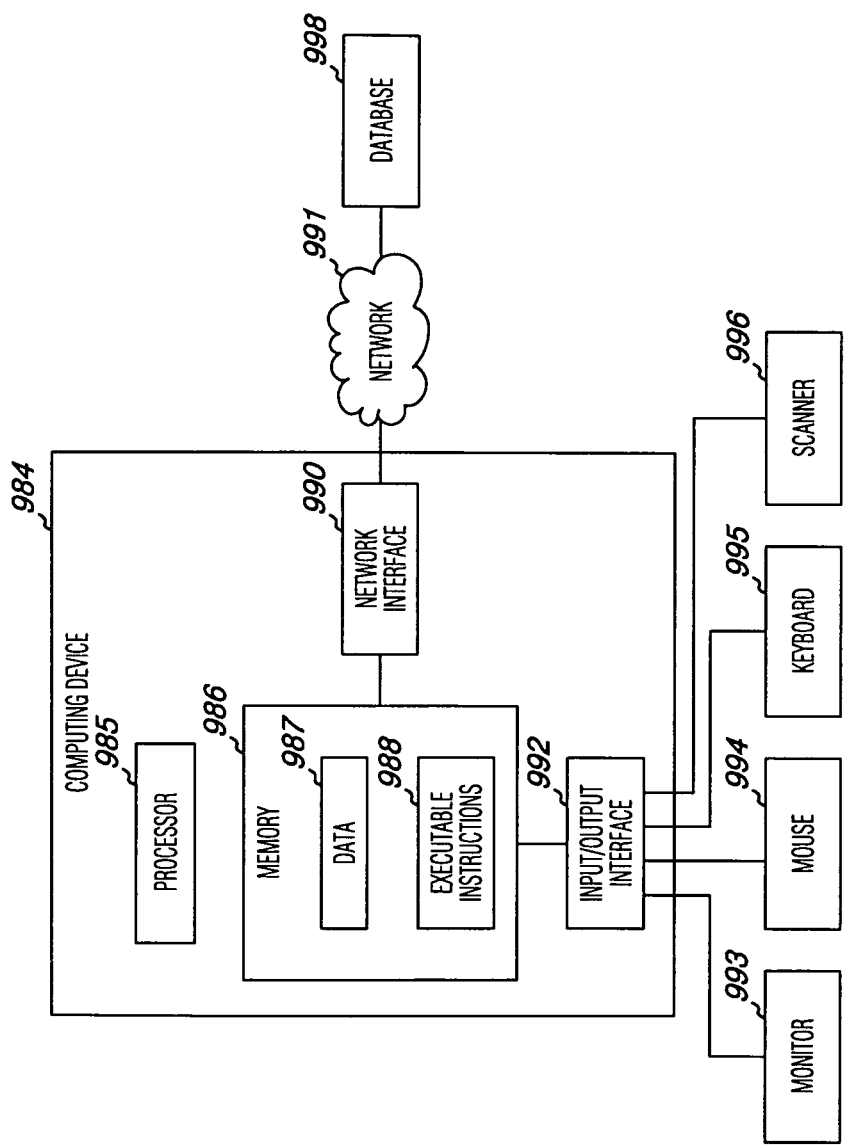
FIG. 9 illustrates a computing device embodiment to perform a method for evaluating a dental condition according to an embodiment of the present disclosure.

Computer analysis may be used to model such material forces during formation from the first sheet (e.g., green phase) to the final dental appliance, for example, by using a computer system such as that illustrated in FIG. 9. Computer modeling and analysis may also be used to predict forces used to achieve desired tooth movement over a course of treatment, and how dental appliance material thickness impacts those forces, such as uniform thickness across the dental appliance and/or localized variations in material thickness. A computer system may be used to simulate force, accounting for material thickness, and in doing so determine customized thickness characteristics for a particular first sheet.

Figure 4A:
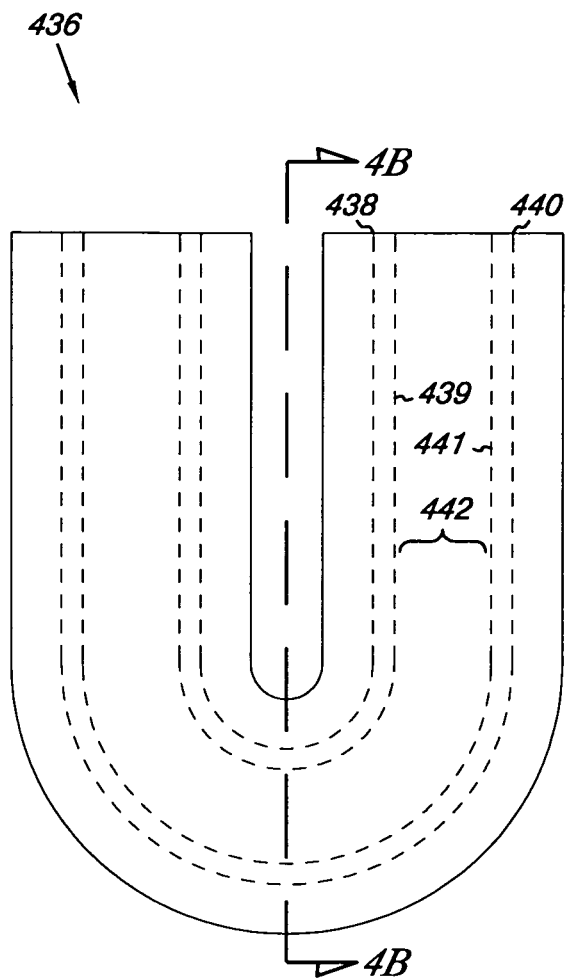
FIG. 4A illustrates an embodiment of a first shape substantially horseshoe-shaped in at least one dimension according to the present disclosure.

FIG. 4A illustrates an embodiment of a first shape 436 substantially horseshoe-shaped in at least one dimension according to the present disclosure. As a patient's dentition, and the polymeric dental appliances for orthodontic dental treatment, are general horseshoe-shaped in at least one dimension, by forming the first shape, e.g., 436, to be substantially horseshoe-shaped in at least one dimension can save some material, compared with a square-shaped, e.g., sheet-like, first shape.

Figure 4B:
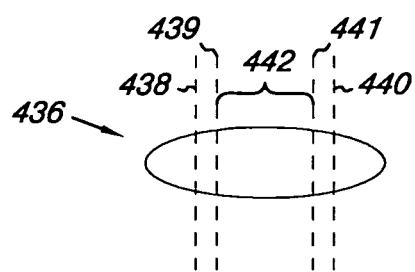
FIG. 4B illustrates a first shape cross section as taken along line 4B-4B of FIG. 4A.

FIG. 4B illustrates a first shape 436 cross section as taken along line 4B-4B of FIG. 4A. The cross section of first shape 436 illustrates that the first shape can be formed to have a non-uniform thickness. However in some embodiments, a first shape that is substantially horseshoe-shaped in at least one dimension can also be formed to be substantially flat, e.g., having a constant thickness.

As one might envision first shape 436 being subsequently thermoformed onto a dentition, the reader can appreciate the location of side portions used to form the sides of a dental appliance generally at lines 438 and 440 on the first shape. The portion of the first shape 436 that will be formed into an occlusal surface of the dental appliance is located generally between lines 439 and 441. The approximate location on the first shape 436 which corresponds then to the transition from the occlusal surface to the side surfaces after thermoforming onto a dentition is generally between lines 438 and 439, and between lines 440 and 441 respectively.

The area between lines 438 and 440 on the first shape corresponds to the location at which the occlusal surface area 442 will exist after thermoforming onto a dentition, as shown in FIGS. 4A and 4B. The thickness of the first sheet 436 need not be uniform in cross section at lines 438 and 440 with respect to the occlusal surface area 442. The thickness of a first shape can vary across its cross section.

The material in some areas of the first shape may be stretched further in forming a dental appliance; therefore, in some instances it can be beneficial to have a greater quantity of thermoset polymer material with which to use in stretching in particular areas of the first shape. For a fixed area of the first shape, and given a constant density of thermoset polymer material, a greater quantity of thermoset polymer material corresponds to a greater thickness in the fixed area.

One skilled in the art will appreciate then, that a thicker first shape provides a greater quantity of thermoset polymer material than a thinner first shape having the same planar area. It will be further appreciated that for a larger jaw size, in order to obtain a dental appliance with the same post-shaping thicknesses, a greater quantity of thermoset polymer material is needed, which can be obtained by using a thicker first shape for a given planar area.

The thickness of the first shape can also vary such that the thermoset polymer material has a greater thickness along the transition lines 438 and 440 and/or along the side surfaces than along an occlusal surface after thermoforming onto the dentition mold. The thickness of the first shape can also vary, in one or more dimensions, such that the thermoset polymer material has a substantially constant thickness after thermoforming onto the dentition mold.

In some embodiments, first shapes may be made in mass quantities, and stored, or may be made on demand according to a particular patient's needs. The first shape may be customized to the shape of a patient's jaw, and with variable thickness to accommodate different crown heights.

Figures 5A, 5B:
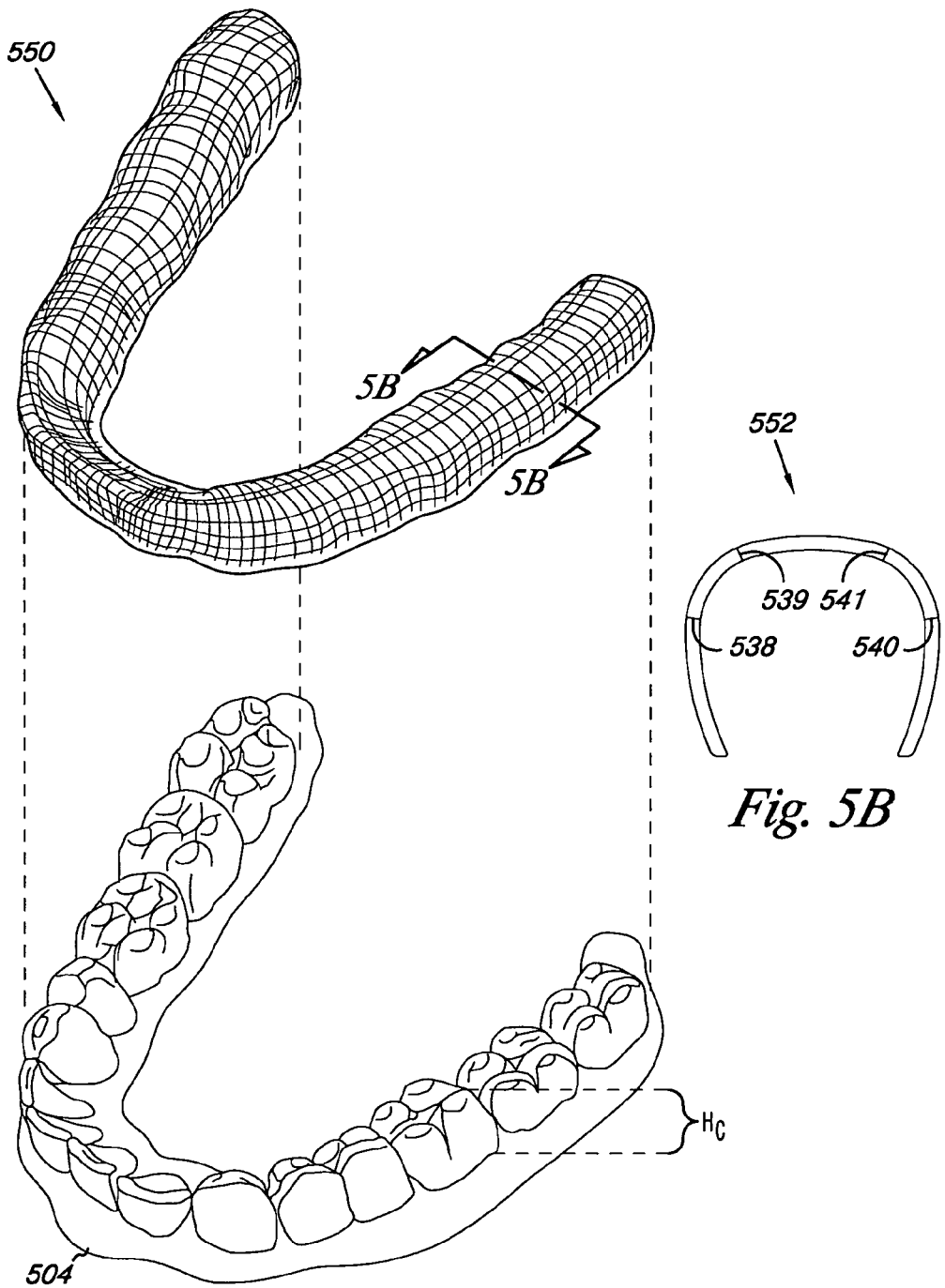
FIG. 5A illustrates an embodiment of a first shape substantially horseshoe-shaped in at least two dimensions according to the present disclosure.
FIG. 5B illustrates a first shape cross section as taken along line 5B-5B of FIG. 5A.

FIG. 5A illustrates an embodiment of a first shape 550 substantially horseshoe-shaped in at least two dimensions according to the present disclosure, and FIG. 5B illustrates the first shape cross section 552 as taken along line 5B-5B of FIG. 5A. FIG. 5A shows a first shape 550 used to form a dental appliance that will correspond to a negative dentition mold of the intended configuration 504.

From FIGS. 5A and 5B, it can be seen that the first shape 550 is formed to be substantially horseshoe-shaped in a first dimension, similar to first shape 436 shown in FIG. 4A. First shape 550 also has a substantially horseshoe-shaped cross section, e.g., be substantially horseshoe-shaped in a second dimension, as can be appreciated from FIG. 5B. Thus, first shape 550 has a substantially horseshoe-shaped cross section 552 along its substantially horseshoe-shape in a first dimension. Lines 538, 539, 540 and 541 shown in FIG. 5B on cross-section 552 correspond in location respectively to lines 438, 439, 440 and 441 shown on first shape 436 in FIGS. 4A and 4B.

Figure 6:
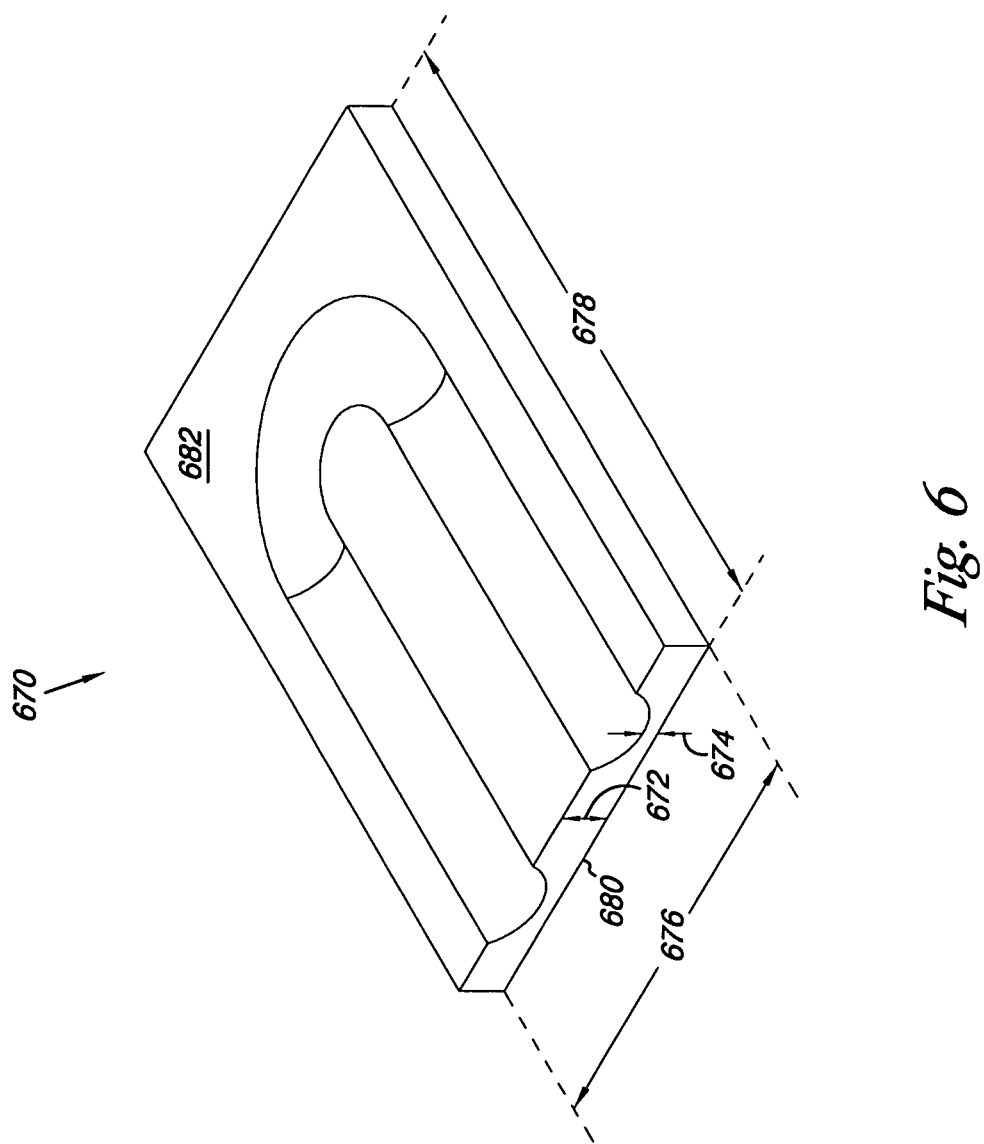
FIG. 6 illustrates an embodiment of a first shape having a variable thickness according to the present disclosure.

FIG. 6 illustrates an embodiment of a first shape 670 having a variable thickness according to the present disclosure. It can be beneficial in some instances to apply force to move teeth at a particular location close to the root. Therefore in such instances, it can be beneficial for a polymeric dental appliance for orthodontic dental treatment to be thicker along a gingival line, in order to provide more material stiffness, and thus more force. It can also be beneficial in some embodiments for a polymeric dental appliance for orthodontic dental treatment to be thinner at the occlusal surface, for example, to minimize the gap created in bite between the jaws when the dental appliance is in place.

The thickness, e.g., 672, of a first shape 670 can vary independently along one or more dimensions, e.g., width 676 and/or length 678. First shape can have one or more flat surfaces, e.g., on a bottom surface 680 and or a top surface 682. Furthermore, the first shape may be formed to have a thickness that varies such that the thermoset polymer material has a greater thickness 672 at locations corresponding to where the gingival lines will be formed, than the thickness 674 corresponding to where an occlusal surface will be formed.

For example, first shape 670 may be formed to have a channel, or groove, within a top surface 682 (as shown) and/or a bottom surface. The channel can, for example, substantially follow a horse-shoe shape of the dentition onto which it may be thermoformed, and may be any suitable cross-section (e.g., semi-circular as shown in FIG. 9).

Figure 7:
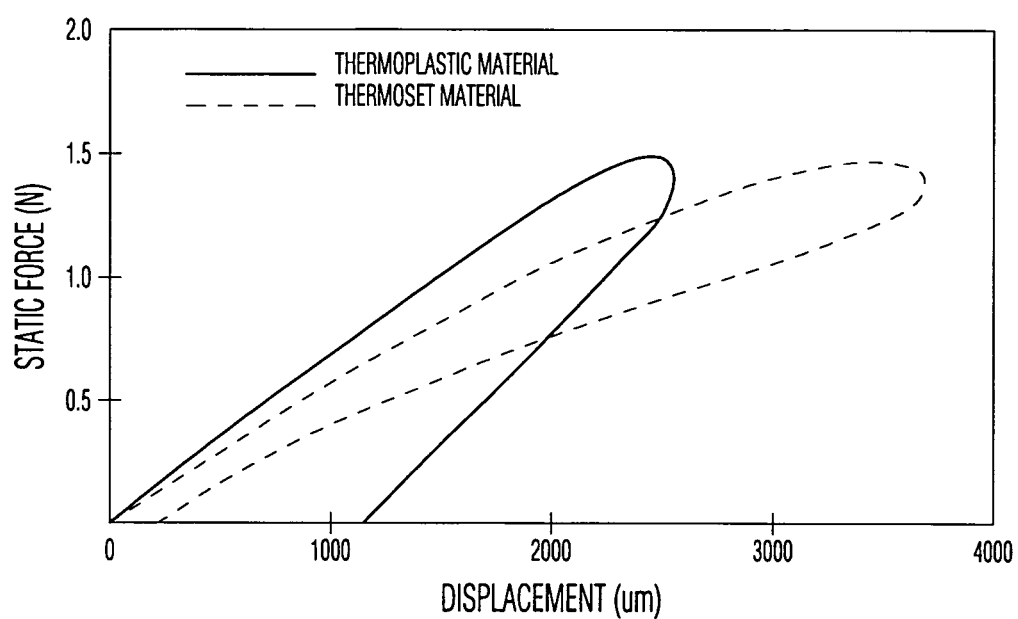
FIG. 7 illustrates working range curves of displacement as a function of static force for a thermoset polymer material in contrast to a thermoplastic material that may be used to form dental appliances of embodiments according to the present disclosure.

FIG. 7 illustrates working range curves of displacement as a function of static force for thermoset polymer material in contrast to thermoplastic material. As will be appreciated, the displacement of thermoset polymer material is generally within a narrower range for a given magnitude of static force, than are expected for thermoplastic material.

That is, that the range of deformation for thermoset polymer material is generally less at a particular applied force, than the range of deformation for thermoplastic material at the same particular applied force, as can be seen by the narrower horizontal width bounded by each curve at the particular applied force. A smaller deformation range can help provide more precise, and thus controllable, locating of teeth positioning.

Figure 8:
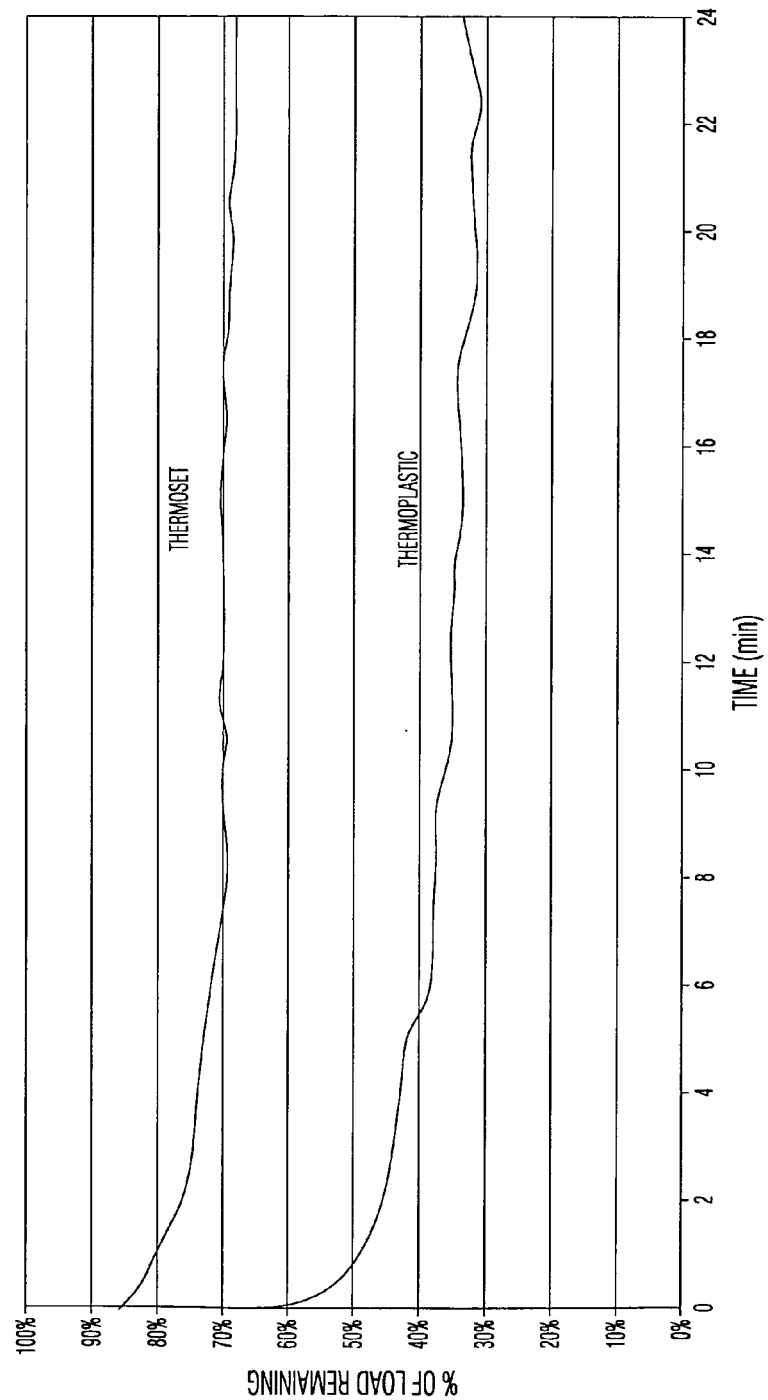
FIG. 8 illustrates stress relaxation performance curves of percentage of load remaining as a function of time for a thermoset polymer material in contrast to a thermoplastic material that may be used to form dental appliances of embodiments according to the present disclosure.

FIG. 8 illustrates stress relaxation performance curves of percentage of load remaining as a function of time for thermoset polymer material (e.g., casting polyurethane) in contrast to thermoplastic material (e.g., polyester, thermoplastic polyurethane). FIG. 8 illustrates thermoset polymer material and thermoplastic material response to relaxation of stress when tested at five percent (5%) strain, a temperature of 37° C., and one hundred percent (100%) relative humidity. As may be observed, the thermoset polymer material exhibits a greater percentage of load remaining over time, indicating less susceptibility to fatigue of the thermoset polymer material as compared to the thermoplastic material.

FIG. 9 illustrates a computing device embodiment to perform a method for evaluating a dental condition according to an embodiment of the present disclosure. The computing device 984 illustrated in FIG. 9, includes a processor 985 and memory 986. Memory 986 can include various types of information including data 987 and computing device executable instructions 988 as discussed herein.

Memory can be used for a variety of different functions in the various embodiments. For example, memory can be used to store executable instructions that can be used to interact with the other components of the computing device and/or network including other computing devices and can be used to store information, such as instructions for manipulating one or more files.

For instance, in some embodiments, a computing device can include executable instructions for saving a number of program and/or data files, such as files, for providing executable instructions that allow for the viewing functionality for viewing scans and/or models, and the data files for the scans and/or digital models. Some executable instructions can, for example, be instructions for saving local scans and/or digital models, scans and/or digital models from another computing device on the network, or a combination of two or more of these.

Additionally, as illustrated in the embodiment of FIG. 9, a system can include a network interface 990. Such an interface can allow for processing on one or more networked computing devices or such devices can be used to transmit and/or receive scans and/or digital models and/or executable instructions for use with various embodiments provided herein.

The network interface 990 can connect the computing device to a network 991. The network 991 can be connected to other computing devices that can execute to make scans and/or digital models of a patient's teeth.

For example, the digital model obtained from a scanner that is interfaced with computing device 984 can be sent on the network 991 to other computing devices. In some embodiments, a number of treatment professionals can have access to the computing devices on the network 991 so they can view and diagnose the dental condition of a user based on the digital model from a remote location.

In the embodiment of FIG. 9, the network 991 is connected to a database 998. The database 998 can, for example, include a case history database that can give access to prior patient's data or other data resources to use in the evaluation and/or treatment process. In such embodiments, treatment professionals that have access to the network 991 and in turn the database 998 can use the database to supplement their evaluation and/or treatment of a user's dental condition.

In some embodiments, the computing device 984 can include executable instructions for estimating the thickness of various portions of the partially cured material. For example, executable instructions can be provided to adjust the thickness of the partially cured material in order to compensate for bending or stretching that may occur during formation of the dental appliance. The data regarding the bending and/or stretching for such analysis can be provided, for example, in memory 986 and/or database 998.

As illustrated in the embodiment of FIG. 9, a system can include one or more input and/or output interfaces 992. Such interfaces can be used to connect the computing device with one or more input and/or output devices.

Such connectivity on the network 991 can allow for the input and/or output of manipulations (e.g., changes to the common file embedded in executable instructions) among other types of information. Although some embodiments may be distributed among various computing devices within one or more networks, such systems as illustrated in FIG. 9, can be beneficial in allowing for the capture, calculation, and/or analysis of the various information discussed herein. For example, the information regarding the adjustment of the thickness of the partially cured material can be provided to a device that is forming the partially cured material, such as via the output interface 992.

Various embodiments include the use of executable instructions to accomplish one or more processes. Such instructions can, for example, be implemented on one or more computing devices and therefore in such embodiments, the executable instructions should be viewed as being computing device executable instructions for implementation by one or more computing devices.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A method for forming a dental appliance, comprising:
partially curing a thermoset polymer material into a semi-solid formable first shape in a first mold;
removing the semi-solid formable first shape from the first mold;
thermoforming the semi-solid formable first shape of thermoset polymer material onto a dentition mold, wherein the first mold is a different mold than the dentition mold; and
fully curing, by application of heat, the thermoset polymer on the dentition mold to complete a molecular cross-linking reaction to form the dental appliance, wherein the dental appliance is a shell having a number of cavities to receive one or more teeth.

2. The method of claim 1, wherein curing the thermoset polymer on the dentition mold includes adding a curative trigger to complete the molecular cross-linking reaction.

3. The method of claim 2, wherein the curative trigger is energy.

4. The method of claim 1, wherein the dental appliance is formed by a process selected from the group including molding, extrusion, and rolling.

5. The method of claim 1, wherein the forming is accomplished by a process selected from the group including compression molding, liquid injection molding, or reaction injection molding.

6. The method of claim 1, wherein the semi-solid formable first shape is substantially horseshoe-shaped in at least one dimension, having proportions at least as large as a top view of the dentition mold.

7. The method of claim 1, wherein the semi-solid formable first shape is substantially horseshoe-shaped in at least two dimensions.

8. The method of claim 1, wherein the semi-solid formable first shape has a uniform thickness.

9. The method of claim 1, wherein the semi-solid formable first shape has a thickness based on jaw size.

10. The method of claim 1, wherein the semi-solid formable first shape has a thickness based on a crown height.

11. The method of claim 1, wherein the semi-solid formable first shape has a non-uniform thickness.

12. The method of claim 11, wherein thickness of the semi-solid formable first shape varies such that the thermoset polymer material has a greater thickness along a gingival line than along an occlusal surface after thermoforming onto the dentition mold.

13. The method of claim 11, wherein thickness of the semi-solid formable first shape varies such that the thermoset polymer material has a substantially uniform thickness after thermoforming onto the dentition mold.

14. The method of claim 11, further comprising partially curing the thermoset polymer material in the semi-solid formable first shape prior to thermoforming.

15. A method for forming a dental appliance, comprising:
delivering a fluid thermoset polymer precursor to a first mold;
partially curing the thermoset polymer precursor in the first mold into a semi-solid formable first shape;
removing the partially cured semi-solid formable first shape from the first mold;
thermoforming the partially cured semi-solid formable first shape of thermoset polymer precursor onto a dentition mold; and
curing, by application of heat, the thermoset polymer precursor on the dentition mold to induce a cross-linking reaction to form the dental appliance, wherein the dental appliance is a shell having a number of cavities to receive one or more teeth.

16. The method of claim 15, wherein curing the thermoset polymer precursor on the dentition mold includes adding a curative trigger to induce the cross-linking reaction.

17. The method of claim 16, wherein the curative trigger is energy.

18. The method of claim 17, wherein the energy to induce the cross-linking reaction is selected from the group including light, radiation, and heat.

19. The method of claim 15, wherein the first mold is configured to form the semi-solid formable first shape includes forming the partially cured thermoset polymer precursor into a flat sheet.

20. A method for forming a dental positioning appliance, comprising:
delivering a fluid thermoset polymer precursor to a first mold having an internal cavity, the internal cavity having a surface corresponding to an external surface of the dental positioning appliance;
partially curing the fluid thermoset polymer precursor in the first mold into a semi-solid formable first shape;
placing a second mold in proximity to the first mold such that a volume for the fluid thermoset polymer precursor remains there between, the second mold being a positive dentition mold having an external surface corresponding to an internal surface of the dental positioning appliance; and
curing the fluid thermoset polymer precursor to cause molecules of the fluid thermoset polymer precursor to irreversibly cross-link into a rigid three dimensional structure to form the dental positioning appliance, wherein the dental positioning appliance is a shell having a number of cavities to receive one or more teeth.

21. The method of claim 20, wherein curing the thermoset polymer precursor includes adding a curative trigger to cause molecules of the fluid thermoset polymer precursor to irreversibly cross-link into a rigid three dimensional structure.

22. The method of claim 21, wherein the curative trigger is energy.

23. The method of claim 20, where the fluid thermoset polymer precursor includes two or more prepolymer components and at least one curative to initiate a chemical reaction involving the two or more components.

24. The method of claim 23, where the fluid thermoset polymer precursor includes at least one or more isocyanates, one or more polyols, and a curative.

* * * * *